(12) United States Patent
Shekhawat et al.

(10) Patent No.: US 8,316,713 B2
(45) Date of Patent: *Nov. 27, 2012

(54) SCANNING NEAR FIELD ULTRASOUND HOLOGRAPHY

(75) Inventors: Gajendra Shekhawat, Arlington Heights, IL (US); Vinayak P. Dravid, Glenview, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/886,929

(22) Filed: Sep. 21, 2010

(65) Prior Publication Data

US 2011/0036169 A1    Feb. 17, 2011

Related U.S. Application Data

(63) Continuation of application No. 12/244,406, filed on Oct. 2, 2008, now Pat. No. 7,798,001, which is a continuation of application No. 11/244,747, filed on Oct. 6, 2005, now Pat. No. 7,448,269, which is a continuation-in-part of application No. 10/913,086, filed on Aug. 6, 2004, now abandoned.

(60) Provisional application No. 60/494,532, filed on Aug. 12, 2003.

(51) Int. Cl.
*G01N 29/04* (2006.01)
(52) U.S. Cl. ............................. 73/603; 73/596; 181/101
(58) Field of Classification Search .................... 73/603, 73/596, 105, 584; 181/101; 331/15, 23, 331/41, 42, 107
See application file for complete search history.

(56) References Cited

U.S. PATENT DOCUMENTS

| | | | |
|---|---|---|---|
| 3,617,754 | A | 11/1971 | Hildebrand |
| 3,690,102 | A | 9/1972 | Du pont et al. |
| 3,889,226 | A | 6/1975 | Hildebrand |
| 4,170,142 | A | 10/1979 | Posakony et al. |
| 4,222,273 | A | 9/1980 | Takahashi et al. |
| 4,267,732 | A | 5/1981 | Quate |
| 4,871,984 | A | 10/1989 | Laton et al. |
| 5,092,336 | A | 3/1992 | Fink |
| 5,262,642 | A | 11/1993 | Wessels et al. |
| 5,410,742 | A | 4/1995 | Yajima |
| 5,503,010 | A | 4/1996 | Yamanaka |
| 5,675,075 | A | 10/1997 | Arnold et al. |

(Continued)

FOREIGN PATENT DOCUMENTS

| | | |
|---|---|---|
| WO | WO 98/08046 | 2/1998 |
| WO | 2012/044811 | 4/2012 |

OTHER PUBLICATIONS

Cuberes et al., Heterodyne Force Microscopy: Nanomapping of Viscoelastic Response at Ultrasonic Speeds, Abstract of STM '99 conference, Jul. 1999, Seoul, Korea.

(Continued)

*Primary Examiner* — J M Saint Surin
(74) *Attorney, Agent, or Firm* — McAndrews, Held & Malloy, Ltd.

(57) ABSTRACT

A high spatial resolution phase-sensitive technique employs a scanning near field ultrasound holography (SNFUH) methodology for imaging elastic as well as viscoelastic variations across a sample surface. SNFUH uses a near-field approach to measure time-resolved variations in ultrasonic oscillations at a sample surface. As such, it overcomes the spatial resolution limitations of conventional phase-resolved acoustic microscopy (i.e. holography) by eliminating the need for far-field acoustic lenses.

36 Claims, 9 Drawing Sheets

U.S. PATENT DOCUMENTS

| | | | |
|---|---|---|---|
| 5,804,708 | A | 9/1998 | Yamanaka et al. |
| 5,821,410 | A | 10/1998 | Xiang et al. |
| 5,840,041 | A | 11/1998 | Petter et al. |
| 5,894,122 | A | 4/1999 | Tomita |
| 6,006,593 | A | 12/1999 | Yamanaka |
| 6,049,728 | A | 4/2000 | Chou |
| 6,094,972 | A | 8/2000 | Yasutake et al. |
| 6,133,795 | A | 10/2000 | Williams |
| 6,353,576 | B1 | 3/2002 | Garlick et al. |
| 6,385,131 | B1 | 5/2002 | Woodsum et al. |
| 6,666,075 | B2 | 12/2003 | Mancevski et al. |
| 6,708,556 | B1 | 3/2004 | Kim et al. |
| 6,747,265 | B1 | 6/2004 | Niewa et al. |
| 6,798,796 | B2 | 9/2004 | Hiroshi et al. |
| 6,831,874 | B2 | 12/2004 | Garlick et al. |
| 6,876,781 | B2 | 4/2005 | Khoury |
| 6,943,924 | B2 | 9/2005 | Marquet et al. |
| 6,983,644 | B2 | 1/2006 | Yamanaka et al. |
| 7,252,661 | B2 | 8/2007 | Nguyen et al. |
| 7,360,404 | B2 | 4/2008 | Reinstadtler et al. |
| 7,448,269 | B2 * | 11/2008 | Shekhawat et al. ............. 73/603 |
| 7,525,661 | B2 | 4/2009 | Mandelis et al. |
| 7,615,738 | B2 | 11/2009 | Kiev |
| 7,665,364 | B2 * | 2/2010 | Su et al. ......................... 73/643 |
| 7,798,001 | B2 * | 9/2010 | Shekhawat et al. ............. 73/603 |
| 7,845,215 | B2 * | 12/2010 | Cantrell et al. ................. 73/105 |
| 7,961,313 | B2 * | 6/2011 | Van Neste et al. ............ 356/311 |
| 2002/0057757 | A1 | 5/2002 | Khoury |
| 2003/0152393 | A1 | 8/2003 | Khoury |
| 2005/0056782 | A1 | 3/2005 | Shekhawat |
| 2006/0037401 | A1 | 2/2006 | Shekhawat et al. |
| 2007/0220978 | A1 | 9/2007 | Su et al. |
| 2008/0276695 | A1 * | 11/2008 | Prater et al. .................... 73/105 |
| 2009/0114024 | A1 | 5/2009 | Shekhawat et al. |
| 2011/0036170 | A1 | 2/2011 | Shekhawat et al. |
| 2011/0120222 | A1 * | 5/2011 | Scholte et al. .................. 73/603 |

OTHER PUBLICATIONS

Kolosov et al., Ultrasonic Force Microscopies—merging ultrasound and SPM to explore nanometre scale mechanics on the nanosecond time scale, Extended Abstract of STM '99 conference, Jul. 1999, Seoul, Korea.

Cuberes et al., Heterodyne force microscopy of PMMA/rubber nanocomposites: nanomapping of viscoelastic response at ultrasonic frequencies, J. Phys. D: Appl. Phys. 33, 2000, pp. 2347-2355, IOP Publishing Ltd.

Geer et al., Nanometer-scale mechanical imaging of aluminum damascene interconnect structures in a lowdielectric-constant polymer, Journal of Applied Physics, Apr. 1, 2002, pp. 4549-4555, vol. 91, No. 7.

Kolosov, UFM shakes out the details at the nanoscopic scale, Materials World, Dec. 1998, pp. 753-754.

European Patent Office, Communication with extended European search report, in Application No. 05808603.4, dated Nov. 14, 2011.

International Search Report corresponding to International Applicational No. PCT/US11/53967, mailed Dec. 1, 2011, 4 pages.

Written Opinion of the International Searching Authority corresponding to International Applicational No. PCT/US11/53967, mailed Dec. 1, 2011, 5 pages.

Hayazawa et al., Metalized tip amplification of near-field Raman scattering, Optics Communications, 2000, Vol. 183, pp. 333-336.

Advanced Characterization Techniques in Optics for Nanostructures, Unlu et al., Dec. 2003, 3 pages.

* cited by examiner 24 hr → incubation 4 hr → incubation

Malaria parasites

Figure 7. Micro-cantilever resonance feedback circuit.

SCANNING NEAR FIELD ULTRASOUND HOLOGRAPHY

CROSS-REFERENCE TO RELATED APPLICATIONS

This application is a continuation of U.S. patent application Ser. No. 12/244,406, filed Oct. 2, 2008, now U.S. Pat. No. 7,798,001, which is a continuation of U.S. patent application Ser. No. 11/244,747, filed Oct. 6, 2005, now U.S. Pat. No. 7,448,269, which is a continuation-in-part of U.S. patent application Ser. No. 10/913,086, filed Aug. 6, 2004, now abandoned which claims benefit from and priority to U.S. Provisional Application No. 60/494,532, filed Aug. 12, 2003. The above-identified applications are hereby incorporated herein by reference in their entirety.

STATEMENT REGARDING FEDERALLY SPONSORED RESEARCH OR DEVELOPMENT

N/A

BACKGROUND OF THE INVENTION

Known acoustic microscopes are used for imaging structures such as integrated circuit (IC) structures. The spatial resolution, w, of an acoustic microscope is given by:

$$w = 0.51 \frac{\partial}{f.NA}$$

where $\theta$ is the speed of sound in the coupling medium, f is the frequency of the acoustic/ultrasonic wave, and N.A. is the numerical aperture of the lens. For a frequency of 1 GHz, the nominal spatial resolution attainable is approximately 1.5 µm. Further, the acoustic microscope has two other major roadblocks in getting high resolution: (1) impedance mismatches and coupling fluid attenuation that is proportional to $f^2$. Higher resolution alternatives for nondestructive mechanical imaging include the atomic force microscope (AFM) or scanning probe microscope (SPM) platforms. A few examples include: force modulation microscopy (FMM) as described by P. Maivald, H. J. Butt, S. A. C. Gould, C. B. Prater, B. Drake, J. A. Gurley, V. B. Elings, and P. K. Hansma in *Nanotechnology* 2, 103 (1991); ultrasonic-AFM as described by U. Rabe and W. Arnold in *Appl. Phys. Lett.* 64, 1423 (1994); and, ultrasonic force microscopy (UFM) as described by O. V. Kolosov, K. Yamanaka in *Jpn. J. Appl. Phys.* 32, 1095 (1993); by G. S. Shekhawat, O. V. Kolosov, G. A. D. Briggs, E. O. Shaffer, S. Martin and R. Geer in Nanoscale Elastic Imaging of Aluminum/Low-k Dielectric Interconnect Structures, presented at the *Material Research Society, Symposium D*, April 2000 and published in *Materials Research Society Symposium Proceedings*, Vol. 612 (2001) pp. 1; by G. S. Shekhawat, G. A. D. Briggs, O. V. Kolosov, and R. E. Geer in Nanoscale elastic imaging and mechanical modulus measurements of aluminum/low-k dielectric interconnect structures, *Proceedings of the International Conference on Characterization and Metrology for ULSI Technology, AIP Conference Proceedings*. (2001) pp. 449; by G. S. Shekhawat, O. V. Kolosov, G. A. D. Briggs, E. O. Shaffer, S. J. Martin, R. E. Geer in *Proceedings of the IEEE International Interconnect Technology Conference*, 96-98, 2000; by K. Yamanaka and H. Ogiao in Applied Physics Letters 64 (2), 1994; by K. Yamanaka, Y. Maruyama, T. Tsuji in Applied Physics Letters 78 (13), 2001; and by K. B. Crozier, G. G. Yaralioglu, F. L. Degertekin, J. D. Adams, S. C. Minne, and C. F. Quate in Applied Physics Letters 76 (14), 2000. Each of these techniques is traditionally sensitive to the static elastic properties of the sample surface.

Recent developments in atomic force microscopes have involved the application of ultrasonic frequency (MHz) vibrations to the sample under study and non-linearly detecting of the deflection amplitude of the tip at the same high frequencies. With this arrangement, which is commonly identified as an ultrasonic force microscope, the ultrasonic frequencies employed are much higher than the resonant frequency of the microscope cantilever. The microscope exploits the strongly non-linear dependence of the atomic force on the distance between the tip and the sample surface. Due to this non-linearity, when the surface of the sample is excited by an ultrasonic wave, the contact between the tip and the surface rectifies the ultrasonic vibration, with the cantilever on which the tip is mounted being dynamically rigid to the ultrasonic vibration. The ultrasonic force microscope enables the imaging and mapping of the dynamic surface viscoelastic properties of a sample and hence elastic and adhesion phenomenon as well as local material composition which otherwise would not be visible using standard techniques at nanoscale resolution.

The drawback of ultrasonic microscopy is that it measures only the amplitude due to ultrasonically induced cantilever vibrations. Moreover, where the sample is particularly thick and has a very irregular surface or high ultrasonic attenuation, only low surface vibration amplitude may be generated. In such circumstances the amplitude of vibration may be below the sensitivity threshold of the microscope in which case measurement is impossible. Moreover, none of the above mentioned techniques measures with high resolution the acoustic phase, which is very sensitive to subsurface elastic imaging and deep defects identification which are lying underneath the surface, without doing any cross sectioning of the samples.

Out-of-plane vibrations created by non-linear tip sample interaction make a very hard elastic contact with the sample surface. Ultrasonic force microscopy (UFM) uses the same method except for a amplitude component rather than a phase contrast. If non-linearity is present in the system, most of the phase contrast will come from the surface and not from a surface/sub-surface phase contrast. Additionally, non-linear tip sample interaction may not provide results for soft materials. Furthermore, in UFM, high mechanical contrast may be acquired with little sub-surface contrast.

BRIEF SUMMARY OF THE INVENTION

The present invention relates to a high spatial resolution phase-sensitive technique, which employs a scanning near field ultrasonic holography methodology for imaging buried or other subsurface structures or variation in the specimen. Scanning near field ultrasound holography (SNFUH) uses a near-field approach to measure time-resolved variations in ultrasonic oscillations at a sample surface. As such, it overcomes the spatial resolution limitations of conventional phase-resolved acoustic microscopy (i.e. holography) by eliminating the need for far-field acoustic lenses.

The fundamental static and dynamic nanomechanical imaging modes for the instrument of the present invention are based on nanoscale viscoelastic surface and subsurface (e.g., buried nanostructure) imaging using two-frequency ultrasonic holography. The scanning near-field ultrasonic technique of the present invention vibrates both the cantilevered tip and the sample at ultrasonic/microwave frequencies. The contact, soft-contact and near-contact modes of tip-sample interaction enable the extraction of the surface acoustic waves signal between the two ultrasonic vibrations.

Perturbations to the phase and amplitude of the surface standing acoustic wave may be locally monitored by the SPM acoustic antenna via lock-in and SNFUH electronic module. As the specimen acoustic wave gets perturbed by buried features, the resultant alteration in the surface acoustic standing wave, especially its phase, is effectively monitored by the SPM cantilever. Thus, within the near-field regime (which enjoys superb spatial resolution), the acoustic wave (which is non-destructive and sensitive to mechanical/elastic variation along its path) is fully analyzed, point-by-point, by the SPM acoustic antenna in terms of its phase and amplitude. Thus, as the specimen is scanned across, a pictorial representation of specimen acoustic wave's perturbation is recorded and displayed, to offer quantitative account of the internal features of the specimen.

Certain embodiments provide contact, soft (e.g., intermittent) contact, and/or near contact modes of operation to identify surface and subsurface (e.g., buried) characteristics of a specimen. Additionally, an SNFUH electronic module extracts surface acoustic phase and amplitude with or without non-linear tip sample interaction These and other advantages and novel features of the present invention, as well as details of an illustrated embodiment thereof, will be more fully understood from the following description and drawings.

Figure 1:
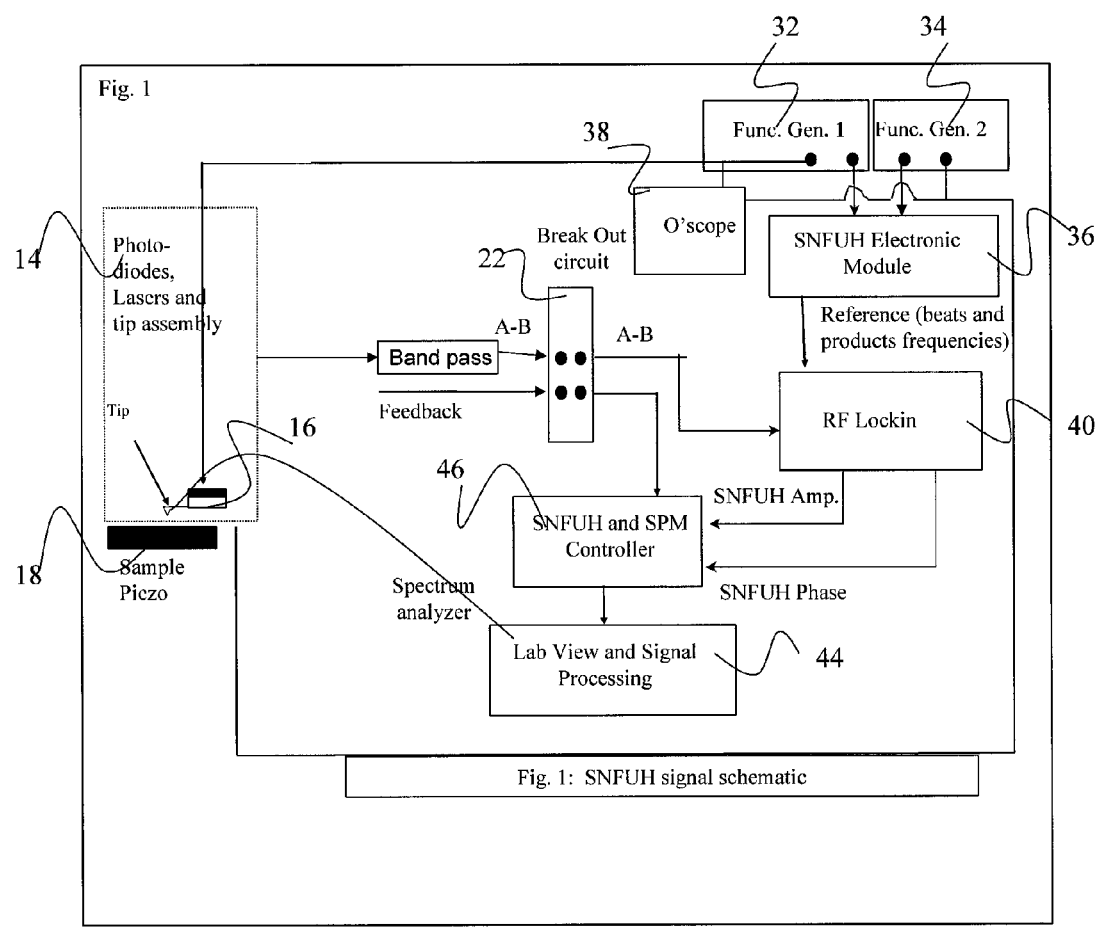
FIG. 1 is a block diagram illustrating the scanning probe microscope with scanning near field ultrasound holography of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments of the present invention are directed to a nondestructive, high resolution, sub-surface nanomechanical imaging system. The system is capable of directly and quantitatively imaging the elastic (static) and viscoelastic (dynamic) response of a variety of nanoscale materials and device structures with spatial resolution of a few nanometers depending on the ultrasonic frequencies. For viscoelastic high resolution sub-surface nanomechanical imaging the target maximum probe frequency is around 5-10 GHz, for example. In an embodiment, the maximum relative phase resolution at this frequency is estimated to be 0.001° leading to a viscoelastic time resolution of less than <1 ps. The instrument of certain embodiments of the present invention operates in a manner similar to commercially available scanning probe microscopes (SPMs) in that quantitative, digital, rastered, nanometer-scale images are obtained of the sample elastic modulus, and sample viscoelastic response frequency. The instrument also provides conventional SPM imaging modes including topography, frictional, and force modulation imaging.

Applications for certain embodiments of the present invention are numerous and represent areas of critical need in Molecular electronics, Nanosystems (NEMS), and Nanotechnology, in general. By combining the nanometer-scale spatial resolution of conventional SPMs with the sub-surface defect identification and imaging capabilities of acoustic or ultrasonic microscopes, the instrument fills a critical need in characterizing and investigating the nanomechanics of nanoscale systems. The SNFUH system and method may be used for: (1) in-vitro imaging of biological specimens, tissues and cells, (2) nanomechanical imaging of buried structures, inclusions in nanocomposites, failure analysis in IC structures and devices, (3) mechanical properties of low-K materials, (4) stress variation in 3D structures and interconnects, (5) flaw imaging in ceramics and quantitative evaluation of mechanical properties, etc.

Certain embodiments of the present invention are based on Nanoscale viscoelastic surface and subsurface (e.g., buried nanostructure) imaging using two-frequency ultrasonic holography. This is essentially a 'scanning near-field' ultrasound technique, where both the cantilevered tip 10 and the sample 12 are vibrated at ultrasonic/microwave frequencies. Contact and soft-contact tip-sample interaction enables the extraction of surface acoustic wave amplitude and phase with high resolution.

In SNFUH mode, perturbation to the standing surface acoustic wave resulting from specimen acoustic wave scattering is monitored by an SPM acoustic antenna. The resulting cantilever deflection merely follows the perturbation to the surface standing acoustic wave, which represents the dissipative lag/lead in the surface response with respect to the tip reference frequency (i.e. the time of flight delay of the specimen acoustic waves reaching the sample surface). Extracting the spatial dependence of this phase term provides image contrast indicative of the relative elastic response of the buried structures, interfaces, and embedded defects to the specimen acoustic wave and thus the resultant perturbation to the standing surface acoustic wave.

Certain embodiments of the present invention provide a system that measures subsurface (e.g., buried) defects, delaminations; cracks; stress migration and etc., while maintaining the high resolution of the atomic force microscope. It utilizes (1) an atomic force microscopy system having a cantilever 14 with a tip 10 at a free end sitting on top of the vibrating device 16 for supplying vibrations to the cantilever at a frequency greater than cantilever resonance frequency, (2) a sample 12 having a vibration device 18 sitting under it for providing high frequency excitations and (3) an optical detector or other detector for detecting movement of the cantilever. It detects the beats, products, additions frequencies and beats, products of their harmonics and modulated waveforms, when the vibrating tip interacts with the vibrating sample, which falls within its detection range. With this embodiment, it is possible to recover surface acoustic wave phase information of the tip-surface mechanical interaction, which allows measurement of viscoelastic properties and enables the application of acoustic holography algorithms for imaging nanoscale sized sub-surface (e.g., buried) defects. The microscopy apparatus utilizes scanning Near Field Ultrasound Holography (e.g., SNFUH) for high resolution nano-mechanical imaging of buried defects and structures.

The surface acoustic wave's amplitude and phase are experimentally extracted from the tip deflection signal via lock-in detection. The phase sensitivity of this measurement is involved in extracting time-resolved mechanical properties of materials as well as potentially enabling subsurface imaging (e.g., buried nanostructures).

Certain embodiments of the present invention detect the phase of transmitted acoustic wave directly at wafer/device surface. Further, certain embodiments of the present invention detect the phase of surface acoustic wave directly at wafer/device surface. Further, certain embodiments of the present invention utilize scanning nanoprobe phase detection so as to eliminate the need for acoustic lenses. The Nanoprobe Acoustic Antenna (AFM Tip) of certain embodiments of the present invention is advantageous because, for example, it provides induction of MHz-GHz nanoprobe mechanical oscillations via high frequency flexural mode excitation, i.e. the mechanical wave guide and the cantilever monitors the phase shifts between tip 10 and sample 12 acoustic/ultrasonic vibrations.

Figure 2:
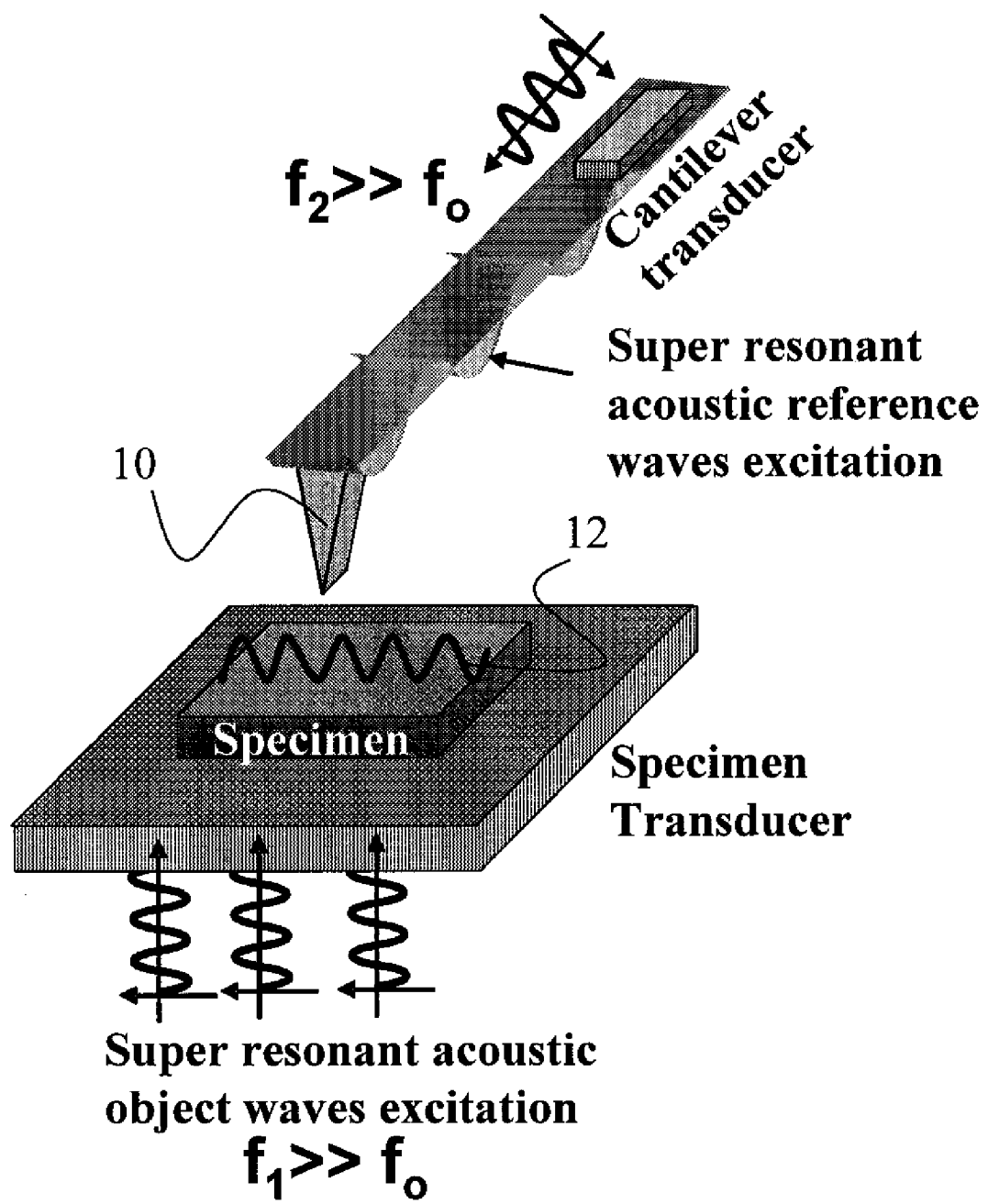
FIG. 2 is an illustration of atomic force microscopy of the present invention with a vibrating cantilever tip and vibrating sample.

As shown in FIGS. 1 and 2, two oscillations are applied to the tip 10 and sample 12 by two matched piezo crystals 16 and 18 attached to the Si substrate of the tip and the base of the sample, respectively. Each piezo 16, 18 is driven by a separate waveform with a SNFUH electronic module 36 providing the input frequency to an RF lockin amplifier 40 for surface acoustic wave (SAW) amplitude and phase extraction. The SNFUH electronic module 36 selects beats, product, and/or addition frequencies for example, to aid in performing holography in contact, soft-contact, and near-contact modes. Additionally, the SNFUH electronic module 36 allows SNFUH to be performed in the linear regime of tip-sample interaction. In an embodiment, the SNFUH electronic module 36 includes a mixer circuit, variable resistor(s), op-amp(s), band pass filter(s), and/or other filters for mixing frequency signals and selecting frequency products, additions and beats, for example.

Any Scanning Probe Microscope (SPM) may serve as the base platform. A signal access module (SAM) 22 is used as the input site for SNFUH, and modulus-calibration signals. The integrated piezo (for high frequency excitation) will enable ultrasonic excitation of higher-order flexural resonances of the cantilever tip 10 to provide the ultrasonic vibration.

The sample ultrasonic vibration is driven by function generator 32. Second function generator 34 applies the sample ultrasonic vibration. The resulting differential output signal from detector is accessed with the signal access module (SAM) 22 and acts as the input to RF lockin amplifier 30 or similar lockin amplifier for extraction of SAW amplitude and phase. The lockin response signal constitutes a SAW amplitude and phase which act as a input into the signal acquisition electronics 46, via the SAM 22, for image display and analysis. The SNFUH electronic module circuit 36 extracts beats, products of fundamental and harmonics, and/or modulated waveform(s), which serve as a reference for a RF lockin amplifier 40 or other lockin amplifier, for example. The differential output of optical detector (A-B) is input, via the SAM 22, into the RF lockin 40. The resulting output constitutes the SNFUH image signal. A computer 44 or other processor running data acquisition/analysis software, such as Lab View or other data acquisition and/or analysis software, acquires both the A-B signal from the digital scope and the lockin. In an embodiment, a switch may be included to select an SNFUH or UFM signal for acquisition, for example.

In an embodiment, the sample piezo consists of an insulator/electrode/piezo/electrode/insulator blanket multilayer (e.g., 10 cm×10 cm) stack. The insulators consist of epoxied machinable ceramics or thin, spin-cast polymer coatings, dependent upon ultrasonic coupling efficiency. The Cr/Au electrodes or other similar electrodes provide electrical contact between the piezo and the second function generator 34. The assembly is counter-sunk into a modified SPM sample mount.

As shown in FIG. 2, using SNFUH, a high frequency acoustic wave is launched from below the specimen 12, while another high frequency acoustic wave is launched at least a slightly different frequency is launched on the SPM cantilever 10. The SNFUH electronic module 36 is used to spatially monitor the phase perturbation to a standing surface acoustic wave, which results from a scattered specimen acoustic wave. The resonant frequency of the cantilever, $f_0$, may be in the 10-100 kHz range, for example.

Figure 7:
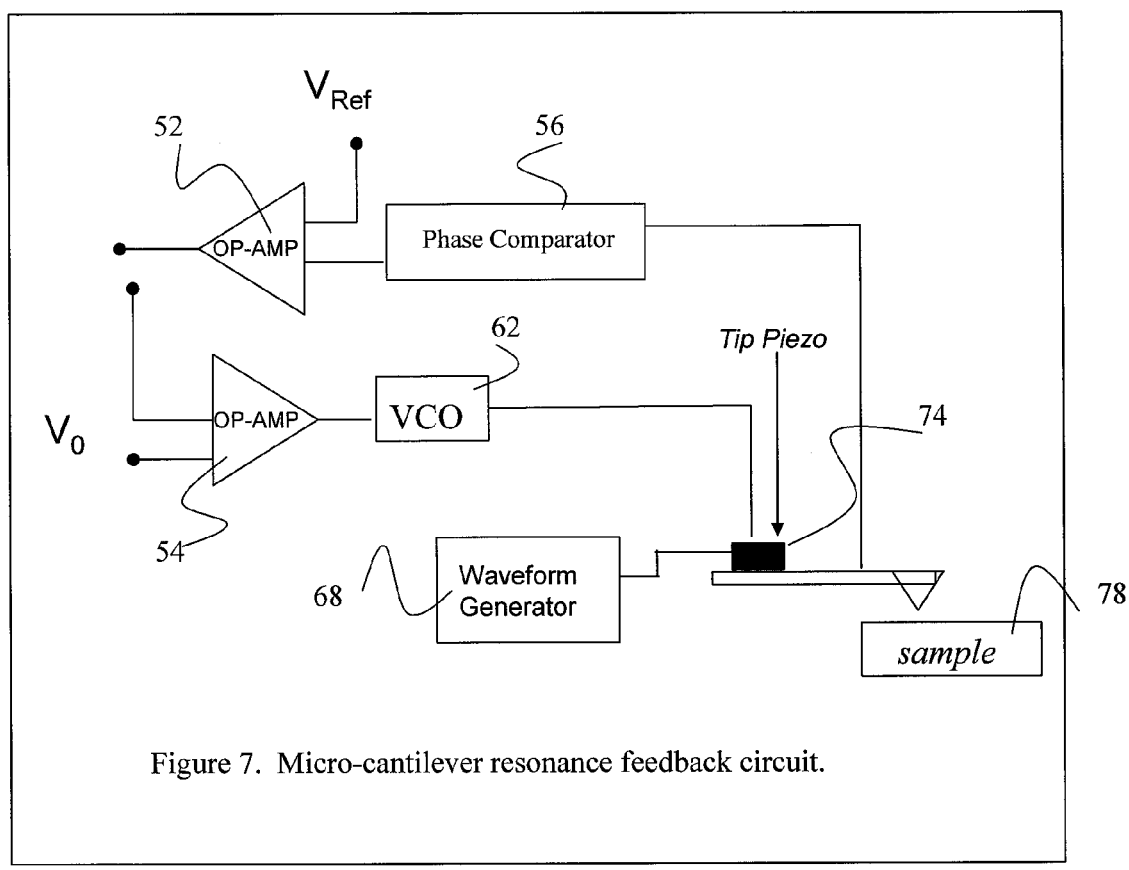
FIG. 7 shows a feedback control circuit used in accordance with an embodiment of the preset invention.

Certain embodiments may also include a feedback circuit, such as the cantilever resonance feedback circuit 50 depicted in FIG. 7. The feedback circuit 50 includes a first op amp (OA) 52, a second op amp (OA) 54, a phase compensator (PC) 56, a voltage-controlled oscillator (VCO) 62, a waveform or function generator 68 and a cantilever tip having a piezo transducer 74 interacting with a sample 78.

For SNFUH operation to be uniquely calibrated across samples, phase of the cantilever may be fixed. In order to fix the phase of the tip, a resonance feedback circuit, said as feedback circuit 50 may be employed. The feedback circuit 50 maintains the tip carrier frequency at resonance and fixes or sets the phase, so that the tip phase is a stable reference for sample phase. For example, at higher frequencies (e.g., 150 MHz-10 GHz), the cantilever easily strays from its resonance, and feedback may be used to maintain the cantilevered tip frequency at resonance. Both the sample and cantilever may maintain their resonance frequencies to generate a high resolution viscoelastic response. In an embodiment, the system may operate in feedback mode with the feedback circuit 50 generating feedback for frequency resonance, or the system may operate without the feedback circuit 50 activated.

In the feedback circuit 50, the voltage-controlled oscillator 62 drives the tip piezo transducer 74. The VCO 62 is connected through the phase compensator 56, which acts as an input to an op amp pair 52, 54 for feedback control. If the cantilever resonance frequency shifts during scanning, the reduction in tip vibration amplitude will reduce the voltage across the piezo transducer on the cantilever. This voltage will cause a shift in the PC 56 output. The shift in PC output will bring the VCO 62 back into resonance.

Figure 8:
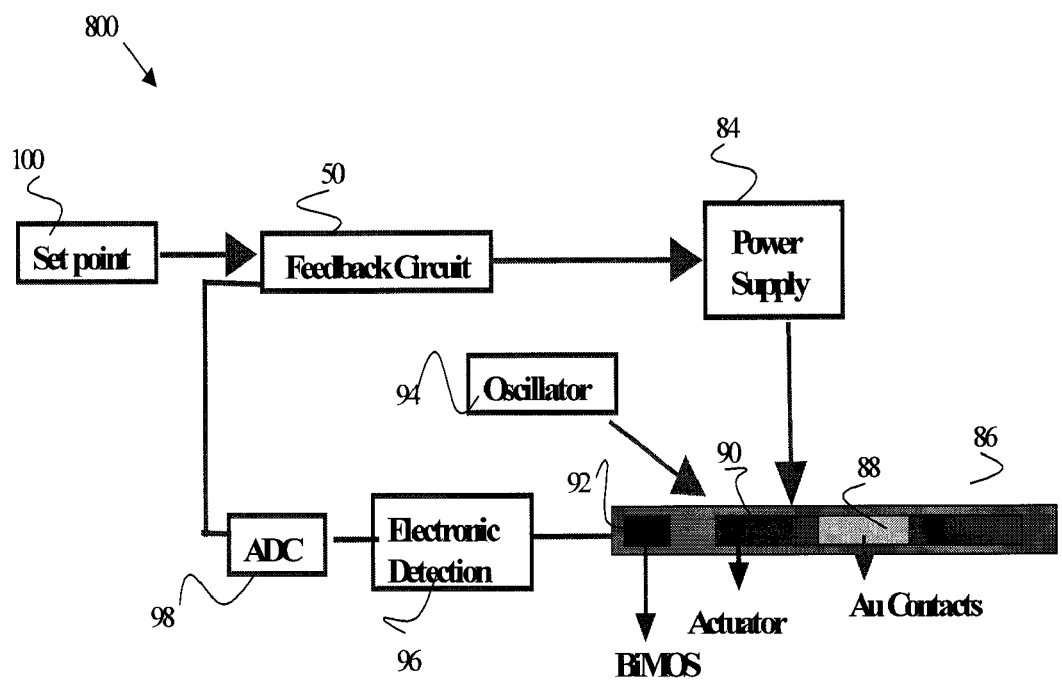
FIG. 8 illustrates the feedback circuit in the context of an embodiment of an electronic readout system used in accordance with an embodiment of the present invention.

FIG. 8 illustrates the feedback circuit 50 in the context of an embodiment of an electronic readout system 800 used in accordance with an embodiment of the present invention. The electronic readout system 800 may be a MOSFET embedded electronic readout, for example. Using embedded MOSFET as electronics feedback may provide a current sensitivity of $\Delta I_d/I_d=10^{-6}$/nm of cantilever bending. Deflection sensitivity of the electronic readout may be of the same order as optical feedback detection, for example. In an embodiment, deflection sensitivity may be approximately three orders of magnitude higher than existing passive and active detection technologies, such as piezoresistive detection. In an embodiment, a high signal-to-noise ratio and minimal 1/f noise allow the MOSFET embedded electronic readout to be used for electronic feedback in SPM's (scanning probe microscopes), for example.

The feedback circuit 50 may be used to control a power supply 84 which supplies power to a piezo 86. The piezo 86 includes contacts, such as Au (gold) contacts 88, as well as an actuator 90 and a BiMOS transistor 92. The piezo 86 is driven by an oscillator 94. Feedback from the oscillating piezo 86 is gathered by the electronic detection unit 96. The feedback signal from the electronic detection unit 96 is converted using the analog to digital converter (ADC) 98 and fed into the feedback circuit 50 for control of the power supply 84. Set point 100 provides a basis or reference for operation of the feedback circuit 50. Feedback from the circuit 50 helps to ensure that the tip and the sample are being vibrated at their respective resonance frequencies, for example.

Figure 3:
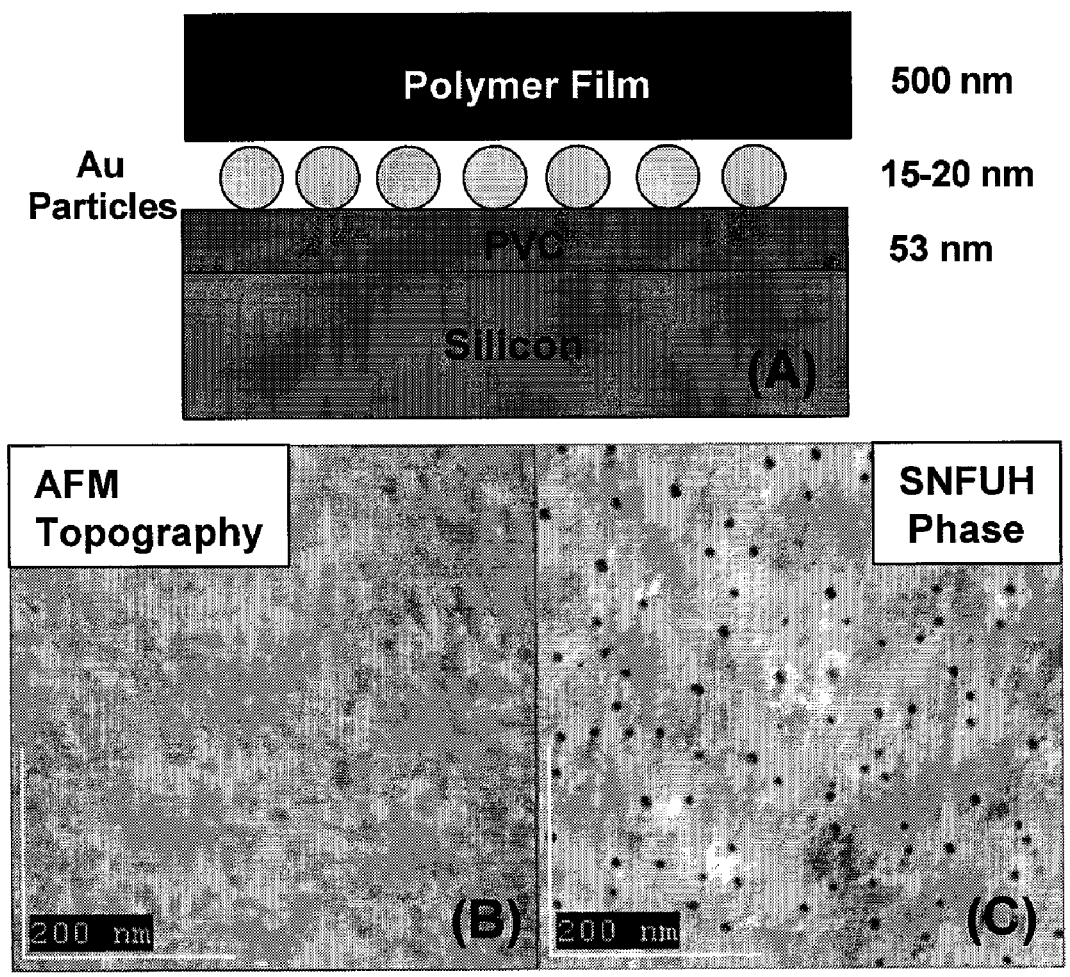
FIG. 3(A) is a schematic illustration of a model nanoparticle system for validation of SNFUH.
FIG. 3(B) shows an AFM (topography) image with a featureless top polymer surface.
FIG. 3(C) shows the phase image of SNFUH revealing buried gold nanoparticles with high definition.

An example of viscoelastic nanomechanical imaging is shown in FIG. 3. FIG. 3(A) shows gold nanoparticles dispersed on a polymer coated substrate are buried under an approximately 500 nm thick polymer layer. Use of a model polymer-nanoparticle composite demonstrates the high lateral spatial resolution and depth sensitivity of the SNFUH approach. A specimen consisting of gold nanoparticles buried deep underneath a polymer cover layer was prepared by dispersing colloidal gold nanoparticles on a polymer (poly(2-vinylpyridine)—PVP) coated silicon substrate. The gold nanoparticles have an average diameter of 15 nm and are well dispersed on the film surface. The nanoparticles were then fully covered with another polymer film about 500 nm thick, as shown schematically in FIG. 3(A). The normal AFM topography scan, FIG. 3(B), shows a smooth featureless surface of top polymeric layer with surface roughness of approximately 0.5 nm. On the other hand, the phase image of SNFUH, FIG. 3(C), shows well-dispersed gold nanoparticles buried approximately 500 nm deep from the top surface. The contrast in the phase image of SNFUH arises from the elastic modulus difference between the polymer and gold nanoparticle, which induces the time dependent phase delay of the acoustic waves reaching the sample surface.

Figure 4:
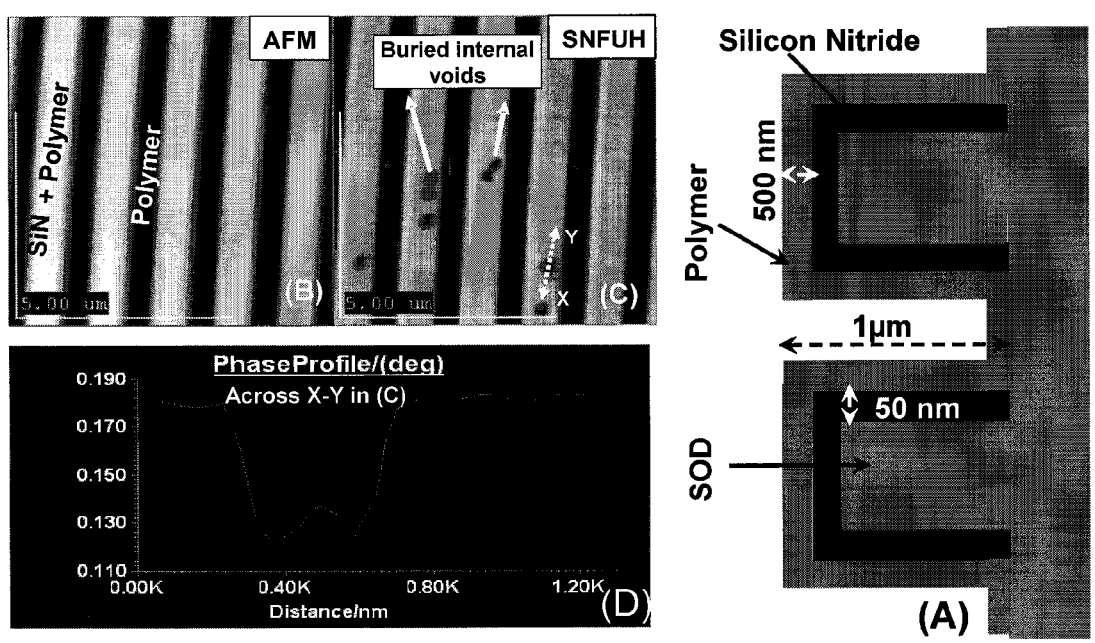
FIG. 4(A) shows a schematic of a model test sample for detecting embedded defects/voiding in shallow trenches.
FIG. 4(B) shows an AFM (topography) image with a uniform coating of dielectric material.
FIG. 4(C) shows a phase image of SNFUH that reveals the surface elastic contrast and embedded voiding in polymer coating over nitride and hardening of the coating at the trench walls.
FIG. 4(D) shows a line profile across a void marked across X-Y.

To demonstrate the efficacy of SNFUH in identifying underlying defects in narrower trenches, shallow trench structures may be fabricated as shown in FIG. 4(A). The trenches are etched in SOD (spin-on-dielectric) with a 50 nm thin layer of LPCVD $Si_3N_4$ as a capping layer and then $Si_3N_4$ is etched down in the 1 μm deep trenches using the wet processing. Trench width in the example is about 400 nm. A 500 nm thick layer of polymer [Benzocyclobutene (BCB)] was spin-coated followed by thermal annealing for curing the polymer.

FIG. 4(A) shows a schematic of series of isolated shallow trench structures. FIG. 4(B) shows a conventional AFM topography image, while FIG. 4(C) is a corresponding (simultaneously recorded) SNFUH phase image. The typical 7.5×7.5 μm² topography scan shows uniform and contiguous polymeric coating on SiN and inside the trenches. On the other hand, the corresponding SNFUH phase image shown in FIG. 4(B) reveals phase contrast reminiscent of embedded voiding within the polymer, and at the SiN-polymer interfaces. The dark contrast in the phase image in polymer coated SiN lines corresponds to voids at polymer-SiN interface, i.e. voiding underneath the contact. The contrast is due to the distinct viscoelastic response from the specimen acoustic wave from the voids, for example. A hardening of the polymer in the trench and its sidewall is also evident in the phase image, which results from thermal annealing and possibly poor adhesion with SOD, for example. FIG. 4(D) shows a line profile of phase across X-Y from FIG. 4(C). A subsurface phase resolution of 50 mdeg may be achieved, for example. Current methods of diagnosis employ destructive approaches such as wet etching followed by SEM imaging, which are undesirable. Thus, SNFUH may be an improved tool-set for such subsurface metrology needs.

The efficacy of SNFUH to imaging embedded or buried sub-structures in biology is demonstrated in FIG. 5, which depicts high resolution and remarkably high contrast arising from malaria parasites inside infected red blood cells (RBCs). FIG. 5 demonstrates early stage direct and real-space in-vitro imaging of the presence of parasites inside RBCs without labels or sectioning of cells, and under physiologically viable conditions. *Plasmodium falciparum* strain 3D7 was cultured in-vitro by a modification of the method of Haldar et al. Parasites were synchronized to within 4 hours using a combination of Percoll purification and sorbitol treatments, cultured to 10% parasitemia, and harvested at the indicated times, for example.

Figure 5A:
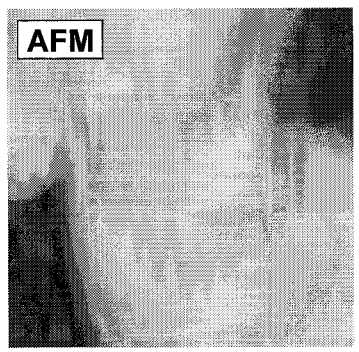
FIG. 5(A) shows an AFM topography of malaria-infected red blood cells.
Figure 5B:
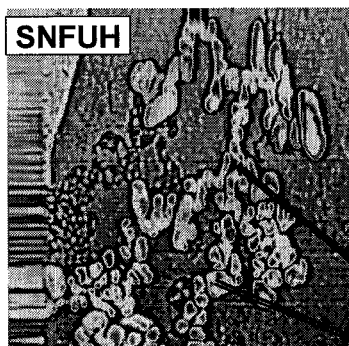
FIG. 5(B) shows an SNFUH phase image from malaria-infected red blood cells.
Figure 5C:
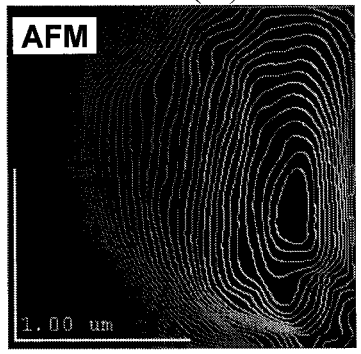
FIG. 5(C) represents an AFM topography of early-stage incubation of parasite infection in malaria-infected red blood cells.
Figure 5D:
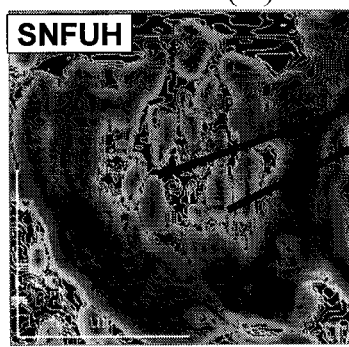
FIG. 5(D) represents an SNFUH phase image of early-stage incubation of parasite infection in malaria-infected red blood cells.

SNFUH imaging may be performed using the near-contact mode method for imaging soft structures, for example. An SNFUH electronic module may be used to bring the cantilever in near-contact mode and then the sample was subsequently scanned over the RBCs while maintaining the near-field regime. FIGS. 5(A) and 5(B) show AFM topography images and SNFUH phase images from infected RBCs, respectively. The AFM topography image shows the typical surface morphology of infected RBC, while the SNFUH phase image shows high contrast from the parasite residing well inside the RBC. In addition to several other features reminiscent of membrane proteins and sub-cellular contents, multiple parasites are clearly evident. In order to further demonstrate the capability of SNFUH for early stage diagnosis of parasite infection, RBCs incubated for only four hours are examined, which is difficult to validate by other non-invasive technique (e.g., fluorescence tagging). FIGS. 5(C) and 5(D) show a pair of images similar to those in FIGS. 5(A) and 5(B).

SNFUH may be sensitive to early stage parasite infection in RBC, as reflected by image contrast consistent with parasite infection, for example.

Figure 6:
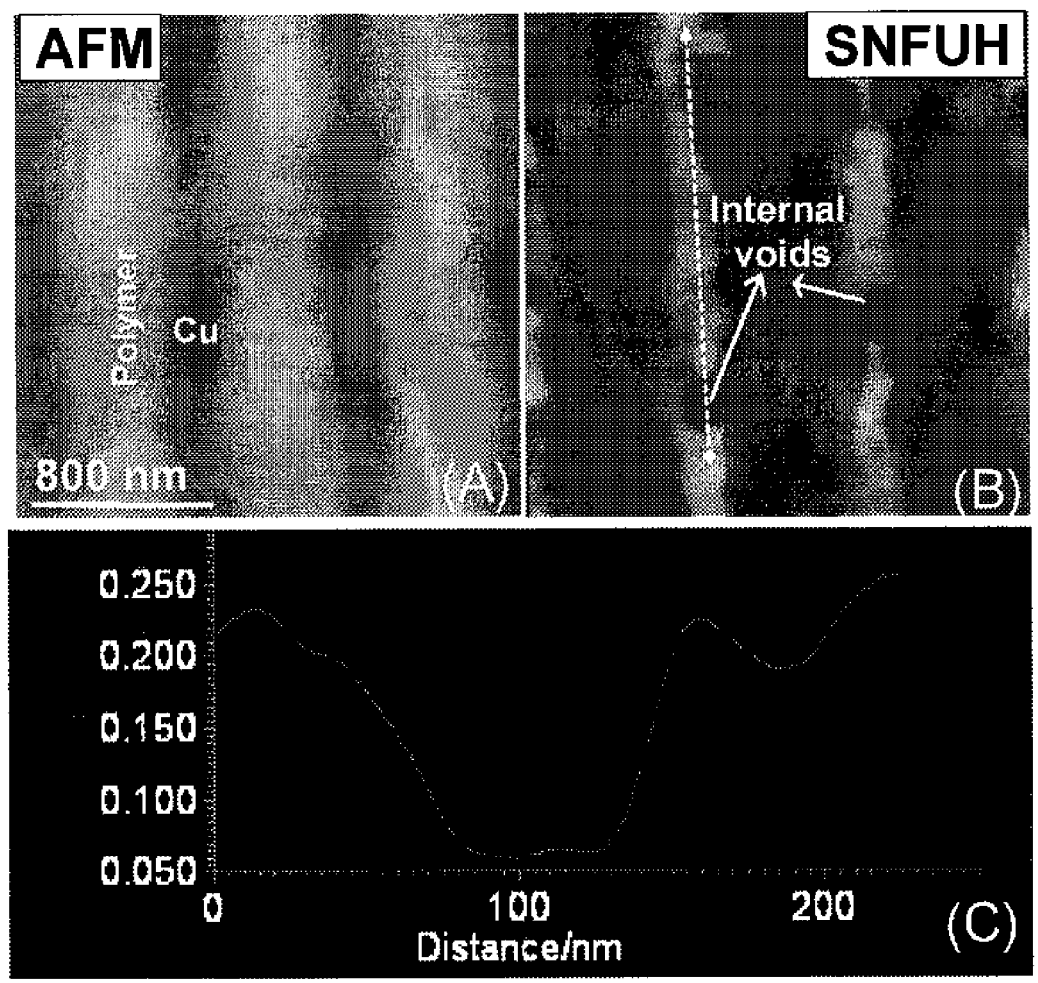
FIG. 6(A) depicts AFM (topography) imaging of a copper-low K dielectric interconnect system.
FIG. 6(B) depicts SNFUH imaging of a copper-low K dielectric interconnect system.
FIG. 6(C) shows a line profile across the voids in FIG. 6(B).

FIG. 6 shows a series of low-K dielectric polymer and copper lines with lateral dimension of about 200 nm for the polymer and around 60 nm for copper. FIG. 6(A) shows the conventional topography image, while FIG. 6(B) is the corresponding (simultaneously recorded) SNFUH phase image. The typical 1400×1400 $nm^2$ topography scan shows uniform and contiguous polymer and copper lines. However, the corresponding SNFUH phase image shown in FIG. 6(B) reveals phase contrast reminiscent of sub-surface voiding in copper lines. FIG. 6(C) shows a line profile across the voids. The dark contrast in the phase image of copper lines corresponds to voids underneath the metal. The presence of this contrast in phase image implies that there is insufficient metal filling at the bottom, i.e. voiding underneath the contact, which undergoes a distinct viscoelastic response. Interestingly, a hardening of the polymeric regions and its sidewall is also evident in the phase image, which results from RIE processing and chemical-mechanical-polishing (CMP). SNFUH may serve as a tool-set for such sub-surface metrology challenges.

Thus, SNFUH may be used to facilitate: (1) quantitative high resolution nanomechanical mapping of subsurface (e.g., buried) structures to identify process-induced mechanical variations and/or nanoscale cohesive defects; (2) nanomechanical viscoelastic (dynamic) imaging to specifically investigate surface and subsurface interfacial adhesive (bonding) response, etc.

Other applications for the system and method of the present invention include: (1) non-destructive imaging of subsurface defects in 3D interconnects and stress migration along the devices due to electrical biasing; (2) non-destructive inspection for interconnect nanotechnology for nanometer-scale resolution, to enable imaging of electro-mechanical defects (e.g. nanotube contacts) and to enable imaging of nanoscale integrity in molecular interconnect assemblies; (3) subsurface nano-cracks, stress, delamination identification in ferroelectrics, ceramics and micromechanical structures and devices; (4) non-destructive defect review and process control in integrated IC materials and devices to provide modulus measurement for soft materials (i.e. porous dielectrics) and to provide void and delamination defect detection to avoid off-line, cross-sectional failure analysis; (5) self assembled monolayers and subsurface defects in biological cells and materials, in-vitro imaging of biological cells, tissues and membranes, nano-bio mechanics and (6) quantitative extraction of elastic modulus with high accuracy.

Figure 9:
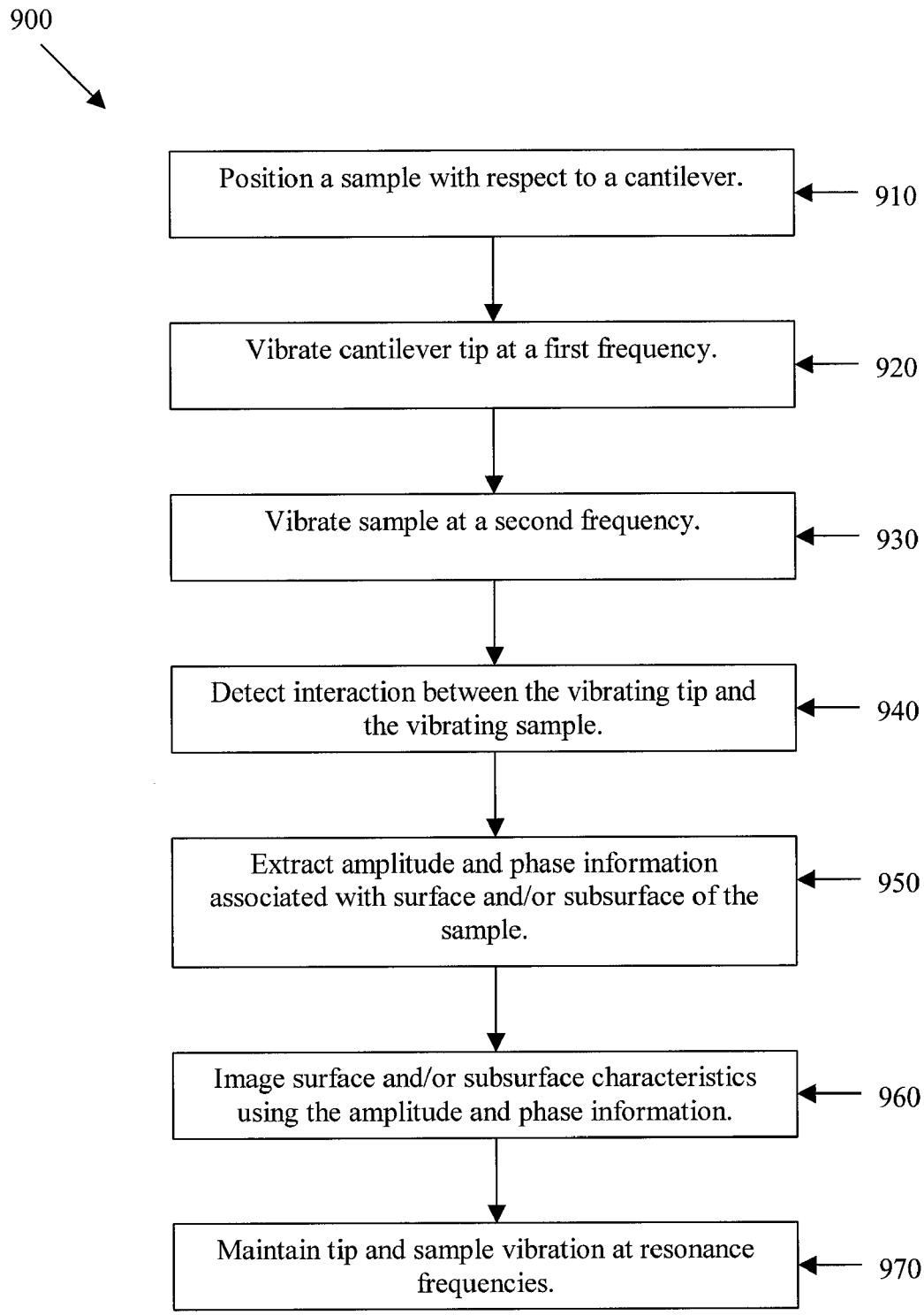
FIG. 9 illustrates a flow diagram for a method for scanning near field acoustic imaging used in accordance with an embodiment of the present invention.

FIG. 9 illustrates a flow diagram for a method 900 for scanning near field holography imaging used in accordance with an embodiment of the present invention. First, at step 910, a sample is positioned with respect to a cantilever for nanomechanical imaging of the sample. Surface and/or subsurface imaging may be performed with respect to the sample, such as a tissue or other sample. At step 920, a tip of the cantilever is vibrated at a first frequency. The frequency may be a first microwave, ultrasonic, or other acoustic frequency, for example. Then, at step 930, the sample is vibrated at a second frequency, such as a second microwave, ultrasonic, or acoustic frequency, for example. In an embodiment, the second frequency vibrates the sample at a frequency that is offset from the first frequency vibrating the tip. In an embodiment, the tip and sample piezos are vibrated at their respective resonance frequencies.

Next, at step 940, interaction between the vibrating tip and the vibrating sample is detected. The interaction may be a physical interaction and/or a non-contact signal interaction between the tip and sample, for example. The interaction may constitute movement of the tip, for example. Tip movement may be provided as a tip deflection signal, for example. In an embodiment, the interaction may include a linear and/or non-linear interaction between the tip and the sample. In an embodiment, SNFUH may be performed using the linear tip-sample interaction in soft contact and near contact mode to obtain the high resolution sub-surface phase. SNFUH may be performed in soft and near contact modes to obtain the sub-surface information, such as buried defects or variations.

At step 950, amplitude and phase information associated with the surface acoustic waves of the sample are extracted. Amplitude and phase information may be extracted from the tip deflection signal using lock in detection, for example. In an embodiment, subsurface mechanical data, such as interfacial bonding, regarding the sample may also be extracted from the tip deflection signal.

At step 960, surface and/or subsurface characteristics of the sample may be imaged using the amplitude and phase information. In an embodiment, a spatial variation of surface and subsurface viscoelastic phase may be imaged, for example. In an embodiment, a characteristic viscoelastic response time of the sample may be defined based on the amplitude and phase information. Then, at step 970, vibration of the cantilever tip is maintained at a tip piezo resonance frequency, and vibration of the sample is maintained at a sample resonance frequency. Feedback, such as electrical feedback, may be provided to maintain the tip resonance frequency and the sample resonance frequency.

In an embodiment, product frequencies may be used with optical detection to obtain biological imaging with high subsurface resolution. The sample and cantilever are excited at their fundamental resonance frequencies (e.g., 1.96 MHz and 3.28 MHz, respectively). Additionally, the individual sample and cantilever carriers are modulated with one or more modulation frequencies (e.g., 25 kHz and 35 kHz, respectively). Next, a combination of a SNFUH electronic module and RF lock in band pass filter outputs a product of the two modulated waveforms. The product output is then fed into a RF lock in amplifier reference input.

Using product frequencies allows improved selection of carrier frequencies. In an embodiment, the larger the frequency of acoustic oscillations, the higher the order of phase contrast that may be obtained from SNFUH images. Thus, smaller features not seen at lower carrier frequencies may be detected using a higher frequency carrier. Additionally, use of product frequencies allows use of non-matching tip and cantilever piezos.

In an embodiment, forces between the cantilever and sample may be controlled during SNFUH operation in near contact mode. Contacting the cantilever with the biological samples may rupture the samples. However, near contact operation allows monitoring and subsurface imaging of soft structures. Near contact mode operation may provide subsurface imaging of soft structures as well as providing quantitative analysis of biological structures, cells and/or tissues, for example.

In an embodiment, beat frequencies may be used to monitor samples in near contact mode. Alternatively, frequency addition may be used for sample monitoring in near contact mode. In an embodiment, harmonics, as well as or in addition to fundamental frequencies, may be used in beat frequency, product frequency, and/or frequency addition (sum) operation. For example, the system may perform optical and/or electronic detection according to a variety of frequency strategies up to 1000 MHz with a very thin film of ZnO.

In an embodiment, cantilever and sample carrier frequencies may be modulated with amplitude modulation. For example, two carriers, a carrier for the cantilever and a carrier for the sample are amplitude modulated individually. In this configuration, the tip-sample assembly may be excited with a higher frequency (with or without matching piezos). Then, an amplitude modulated waveform may be obtained from both the cantilever and sample and input to a SNFUH electronic module. The output of the electronic module is a product/difference/addition frequency. A beat or difference frequency is a difference between modulation frequencies, for example.

In an embodiment, an electronic readout device may be implemented with the sample monitoring system. An example of such a readout device may be the readout device described in U.S. patent application Ser. No. 10/996,274, filed on Nov. 23, 2004, entitled "Method and System for Electronic Detection of Mechanical Perturbations Using BiMOS Readouts", which is herein incorporated by reference. In an embodiment, using a readout circuit allows product frequencies to be used without modulation since operation is not limited by response time as with optical photodiodes, for example.

In an embodiment, use of electronic detection eliminates optical detection of amplitude and phase removes or eases limitations imposed by a photo-detector response frequency, such as a 1 MHz photo-detector response frequency. Electronic detection aids in fabricating multi-active probes with on-chip integrated piezo-actuator (e.g., ZnO) and embedded MOSFET feedback electronics. Additionally, electronic detection does not limit detection of subsurface features based on beat frequency. Multiples of frequencies may be used to enhance both amplitude and subsurface phase contrast, and thus the viscoelastic response. Enhanced viscoelastic response results in enhanced phase contrast from features less than 50 nm, for example, which may be difficult to detect using only beat frequencies.

Thus, certain embodiments provide a scanning near field ultrasound holography (SNFUH) technique to image high resolution buried nanostructures, defects, 3D tomography, identification of individual layers in multilayer thin film stacks and dopant mapping, for example. Certain embodiments integrate three approaches: a combination of scanning probe microscope platform (which enjoys excellent lateral and vertical resolution) coupled to micro-scale ultrasound source and detection (which facilitates "looking" deeper into structures, section-by-section) and a holography approach (to enhance phase resolution and phase coupling in imaging). Certain embodiments provide near field, ultrasonic holography, near field microwave holography, or other near field acoustic holography for surface and subsurface imaging in nano- and micro-specimens, such as biological, mechanical, and electrical specimens. Certain embodiments allow SNFUH imaging using linear and/or non-linear interactions between cantilever and specimen in contact, soft contact and/or near contact mode, for example.

As a result, the technique allows subsurface flaw imaging in nano- and micro-composites, MEMS, CMOS, and heterostructures, for example. The technique also provides in-vitro imaging of biopolymer, biomaterials and biological structures (e.g. viewing cell-membrane or implant-bio interface). Additionally, certain embodiments detect voiding and subsurface defects in low-K dielectric materials and interconnects, as well as stress migration and defect analysis in 3D interconnects and MEMS. Certain embodiments facilitate dopant profiling and modulus mapping in non-contact mode and also provide non-invasive monitoring of molecular markers/tags-signal pathways, for example.

In an embodiment, a high frequency (e.g., on the order of hundreds of MHz) acoustic wave is launched from the bottom of the specimen, while another wave is launched on the AFM cantilever. These acoustic waves are mixed together through a SNFUH electronic module, which includes a combination of various filters, mixers, feedback electronics and electronic components used to obtain a desired product and addition of fundamental resonances and related harmonics (in addition to difference frequencies). The resulting mixed wave is monitored by the AFM tip, which itself acts as an antenna for both phase and amplitude. As the specimen acoustic wave gets perturbed by buried features, especially its phase, the local surface acoustic waves are very effectively monitored by the AFM tip. Thus, within the near-field regime (which enjoys superb lateral and vertical resolution), the acoustic wave (which is non-destructive and sensitive to mechanical/elastic variation in its "path") is fully analyzed, point-by-point, by the AFM acoustic antenna in terms of phase and amplitude. Thus, as the specimen is scanned across, a pictorial representation of acoustic wave's perturbation is fully recorded and displayed, to offer a "quantitative" account of internal microstructure of the specimen.

The SNFUH system is operational in the linear and near-contact regime of tip-sample interaction and proves effective for in-vitro imaging of biological cells and tissues using the SNFUH electronic module, for example.

Thus, certain embodiments provide an electronic readout based on an embedded MOSFET to detect product frequencies, which is thereby not limited by an optical detector. Moreover, electronic readout may help in building a parallel SNFUH system for industrial application. In addition, a Brillion Zone Scattering technique may be used to map the modules of any surface in non-destructive way with greater efficiency than other methods.

Certain embodiments may be applied to microelectronics, especially as an advanced nanoscale surface and sub-surface metrology tool-set. Further, certain embodiments provide imaging for Nanoelectronics, reliability and failure analysis in Microsystems (MEMS), and Nanotechnology, in general, and especially biomolecular interconnects and BioMEMS. Additionally, certain embodiments provide in-vitro imaging of biological structures without having to "open-up" internal structures. By combining the nanometer-scale spatial resolution of conventional SPMs with the sub-surface imaging capabilities, certain embodiments may characterize the surface defects and structures with high resolution and will have further potential for developing nanoscale non-invasive 3D tomography, for example.

Scanning Near Field Ultrasound Holography (SNFUH) may be used, for example, in near contact and contact mode with product frequencies for the following structures and devices: (1) Investigating mechanical uniformity and process-induced mechanical modification of materials in integrated circuit (IC) structures and MEMS; (2) Real-time in-vitro biological imaging of red blood cells infected with malaria parasites; (3) Voiding in copper interconnects and (4) Non-invasive monitoring of nanoparticles buried under polymeric films. Such capabilities may complement cross-sectional imaging techniques such as SEM-EDS (scanning electron microscope-energy dispersive spectroscopy), TEM-EDS (transmission electron microscope-energy dispersive spectroscopy), TEM-EELS (transmission electron microscope-electron energy-loss microscopy), and ex situ STM (scanning tunneling microscopy) to investigate the nanomechanics and subsurface imaging of material interfaces, the uniformity of conformally deposited coatings, and mechanical defects in multilayer structures, for example.

Many other applications of the present invention as well as modifications and variations are possible in light of the above teachings. While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A scanning near field ultrasound holography method for surface and subsurface imaging, comprising:
vibrating a cantilevered tip at a first ultrasonic frequency;
vibrating a sample at a second ultrasonic frequency, the first ultrasonic frequency being different from the second ultrasonic frequency;
detecting movement of the cantilevered tip interacting with the vibrating sample to provide a tip deflection signal; and
extracting surface acoustic wave amplitude and phase information associated with the surface and subsurface of the sample using lock in detection.

2. The method of claim 1, wherein the method is used by a system that is configured for near field holography.

3. The method of claim 1, wherein the method is used by a system that is configured for near field holography for nano-mechanical imaging of buried defects and structures.

4. The method of claim 1, wherein the method is used by a system that is configured to recover surface acoustic wave phase information of an interaction between the cantilevered tip and the surface, and wherein the recovered information allows measurements of viscoelastic properties and enables application of acoustic holography algorithms for imaging nano-scale sized subsurface defects.

5. The method of claim 1, wherein the extracting step comprises extracting surface acoustic wave amplitude and phase information associated with the surface and subsurface of the sample using lockin detection and a scanning near field ultrasound holography electronic module.

6. The method of claim 1, wherein a scanning near field ultrasound holography electronic module extracts beats that serve as a reference for a lockin amplifier.

7. The method of claim 1, wherein the lockin amplifier receives beats extracted by an electronic module, the beats serving as a reference for the lockin amplifier, and wherein the lockin amplifier receives a differential output of an optical detector, the optical detector being used to detect movement of a cantilever with the cantilevered tip.

8. The method of claim 1, wherein a scanning near field ultrasound holography electronic module extracts products of fundamental and harmonic signals that serve as a reference for a lockin amplifier.

9. The method of claim 1, wherein the lockin amplifier receives products of fundamental and harmonic signals extracted by an electronic module, the products serving as a reference for the lockin amplifier, and wherein the lockin amplifier receives a differential output of an optical detector, the optical detector being used to detect movement of a cantilever with the cantilevered tip.

10. The method of claim 1, wherein the second ultrasonic frequency vibrates the sample at a frequency offset from the first ultrasonic frequency.

11. The method of claim 1, wherein the extracting step includes extracting subsurface mechanical data regarding the sample from the tip deflection signal.

12. The method of claim 1, wherein the subsurface mechanical data includes interfacial bonding.

13. The method of claim 1, comprising imaging a spatial variation of surface and subsurface viscoelastic phase.

14. The method of claim 1, comprising defining a characteristic viscoelastic response time of the sample based on the amplitude and phase information.

15. The method of claim 1, comprising maintaining the vibration of a cantilever tip piezo at a tip piezo resonance frequency and the vibration of the sample at a sample resonance frequency.

16. The method of claim 15, comprising providing electrical feedback to maintain the tip piezo resonance frequency and the sample resonance frequency.

17. The method of claim 1, wherein beat frequencies, product frequencies or frequency addition are used to generate the tip deflection signal to monitor the sample in near contact mode.

18. The method of claim 1, comprising operating in near contact mode without contact between the cantilevered tip and the sample.

19. The method of claim 1, wherein the vibrating of the cantilevered tip is facilitated by a first piezo crystal attached to a substrate of the cantilevered tip, wherein the vibrating of the sample is facilitated by a second piezo crystal attached to a base of the sample, and wherein the first piezo crystal and the second piezo crystal are matched.

20. The method of claim 1, wherein the cantilevered tip and the sample are vibrated at fundamental resonance frequencies and related harmonics.

21. A scanning near field holography method for surface and subsurface imaging comprising:
vibrating a cantilevered tip at a first microwave frequency;
vibrating a sample at a second microwave frequency, the first microwave frequency being different from the second frequency;
detecting movement of the cantilevered tip interacting with the vibrating sample to provide a tip deflection signal; and
extracting surface acoustic wave amplitude and phase information associated with the subsurface of the sample from the tip deflection signal using lock in detection.

22. The method of claim 21, wherein the method is used by a system that is configured for near field holography.

23. The method of claim 21, wherein the method is used by a system that is configured for near field holography for nano-mechanical imaging of buried defects and structures.

24. The method of claim 21, wherein the method is used by a system that is configured to recover surface acoustic wave phase information of an interaction between the cantilevered tip and the surface, and wherein the recovered information allows measurements of viscoelastic properties and enables application of acoustic holography algorithms for imaging nano-scale sized subsurface defects.

25. The method of claim 21, wherein the extracting step comprises extracting SAW amplitude and phase information associated with the subsurface of the sample from the tip deflection signal using lock in detection and a scanning near field ultrasound holography electronic module.

26. The method of claim 21, comprising:
using a linear interaction between the cantilevered tip and the sample to detect beats at the surface of the sample; and extracting phase and amplitude signals for the first microwave frequency and the second microwave signal.

27. The method of claim 21, comprising imaging the surface and subsurface of the sample based on the amplitude and phase information of the tip deflection signal.

28. The method of claim 21, wherein the cantilevered tip and the sample are vibrated at fundamental resonance frequencies and related harmonics.

29. An atomic force microscopy system, comprising:
a cantilever, wherein the cantilever includes a tip at an end of the cantilever;
a device configured to supply vibrations at a first frequency to the cantilever to generate vibrations at the tip; and
a detector configured to detect movement of the tip based on an atomic force between the tip and a surface of a sample, wherein the sample is vibrated at a second frequency that is different from the first frequency, wherein the system is configured for near field holography for nano-mechanical imaging of buried defects or buried structures.

30. The system of claim 29, wherein the system is configured for near field holography.

31. The system of claim 29, wherein the system is configured to perform nondestructive imaging of the buried defects or the buried structures at a nanometer-scale resolution when the tip is operated in near contact mode.

32. The system of claim 29, wherein the system is configured to recover surface acoustic wave phase information of an interaction between the tip and the surface, and wherein the recovered information allows measurements of viscoelastic properties and enables application of acoustic holography algorithms for imaging nano-scale sized subsurface defects.

33. The method of claim 1, comprising:
selecting, by a circuit, at least one of beat frequencies and product frequencies that serve as a reference for use with the lock in detection, the circuit being communicatively disposed between at least one function generator and a lockin amplifier.

34. The method of claim 21, comprising:
selecting, by a circuit, at least one of beat frequencies and product frequencies that serve as a reference for use with the lock in detection, the circuit being communicatively disposed between at least one function generator and a lockin amplifier.

35. The system of claim 29, comprising:
a function generator configured to generate a signal of at least one of the first microwave frequency and the second microwave frequency; and
a circuit configured to select at least one of beat frequencies and product frequencies that serve as a reference for use with the lock in detection, the circuit being communicatively disposed between the function generator and a lockin amplifier.

36. The system of claim 29, wherein the tip and the sample are vibrated at fundamental resonance frequencies and related harmonics.

* * * * *